United States Patent [19]

Pelta

[11] Patent Number: 4,971,037

[45] Date of Patent: Nov. 20, 1990

[54] SURGICAL RETRACTOR SUPPORT

[75] Inventor: Samuel Pelta, Philadephia, Pa.

[73] Assignee: Pilling Co., Fort Washington, Pa.

[21] Appl. No.: 246,350

[22] Filed: Sep. 19, 1988

[51] Int. Cl.[5] .............................................. A61B 17/02
[52] U.S. Cl. ..................................... 128/20; 403/390; 403/55
[58] Field of Search .................. 128/20, 346; 269/322, 269/45, 72, 323; 403/55, 390, 396, 54, 175, 177, 184, 218, 373; 24/525, 486

[56] References Cited

U.S. PATENT DOCUMENTS

| | | | |
|---|---|---|---|
| 3,046,040 | 7/1962 | Luper | 403/390 |
| 3,221,743 | 12/1965 | Thomson et al. | 128/20 |
| 3,227,156 | 1/1966 | Gauthier | 128/20 |
| 3,810,462 | 5/1974 | Szpur | 269/322 |
| 4,066,371 | 1/1978 | Chapman | 403/218 |
| 4,280,769 | 7/1981 | Ceglowski | 403/218 |
| 4,398,129 | 9/1982 | Conforti | 403/218 |
| 4,461,284 | 7/1984 | Fackler | 128/20 |
| 4,617,916 | 10/1986 | LeVahn et al. | 128/20 |
| 4,718,151 | 1/1988 | LeVahn et al. | 128/20 |

FOREIGN PATENT DOCUMENTS

| | | | |
|---|---|---|---|
| 1045181 | 4/1955 | Fed. Rep. of Germany | 403/340 |
| 660318 | 11/1951 | United Kingdom | 403/39 |

OTHER PUBLICATIONS

"A History of Surgical Retraction and Competitive Analysis", Minnesota Scientific, Inc. 7/86.

*Primary Examiner*—Edward M. Coven
*Assistant Examiner*—Mark S. Graham
*Attorney, Agent, or Firm*—Howson & Howson

[57] ABSTRACT

A table-mounted surgical retractor support includes a wishbone-shaped structure comprising two identical rods which are separately attachable to a clamp located at the end of a supporting rod. The supporting rod is, in turn, connected to a similar clamp located at the top of a table-mounted post. The two parts of the wishbone structure are small enough to be sterilized conveniently.

The wishbone rods cannot be rotated in their clamp, nor can the supporting rod be rotated in its clamp. However, the wishbone clamp, when loosened, allows rotation of the wishbone structure about the supporting rod axis and also about an axis mutually perpendicular to the supporting rod axis and the wishbone plane. Likewise the supporting rod clamp allows rotation of the supporting rod about the axis of the post and about an axis mutually perpendicular to the supporting rod and the post. Each clamp is designed to apply a shear to the rod on which it is supported, thereby achieving a tight clamping action.

7 Claims, 3 Drawing Sheets

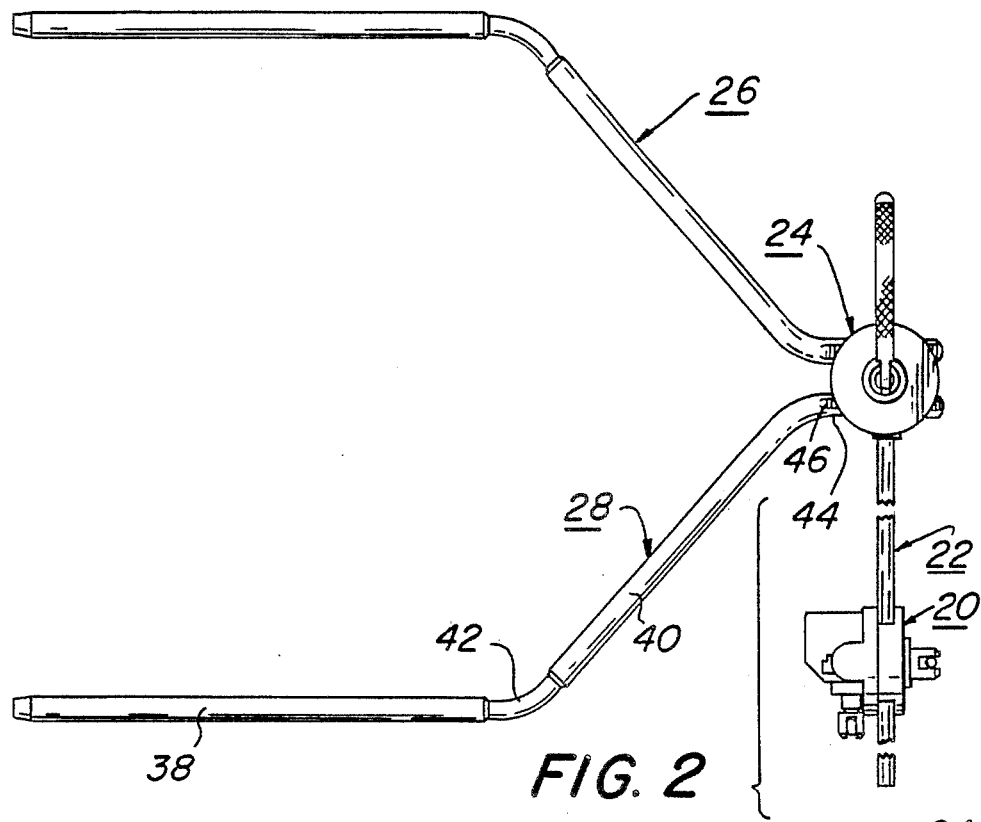
FIG. 2
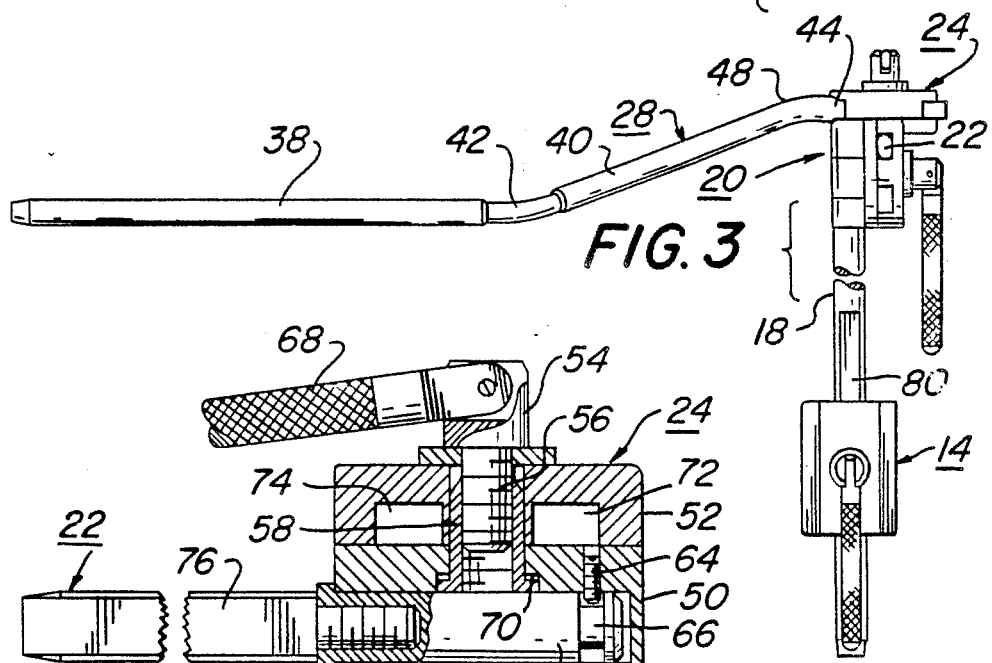
FIG. 3
FIG. 4

(51) Int. Cl.⁵ ... not shown

SURGICAL RETRACTOR SUPPORT

BRIEF SUMMARY OF THE INVENTION

This invention relates to surgical retractors, and specifically to a table-mounted retractor support to which multiple retractor blades may be attached by clamps.

The invention has utility in various kinds of surgery, and especially in major abdominal vascular procedures involving the aorta, the iliac arteries and their branches.

In general, mechanical retractor supports reduce the number for surgical assistants required and eliminate the fatigue associated with manual retractor handling. Table-mounted retractor supports are frequently preferred over patient-supported retractor rings because the table-mounted supports provide better exposure to the surgical site, thereby allowing speedier operative procedures and reducing post-operative pain and complications.

A number of table-mounted retractor supports have been proposed. Many of these are in the form of frames held by multiple supports from the side rails of an operating table. The support most closely related to the present invention is the support described in U.S. Pat. No. 4,617,916, issued on Oct. 21, 1986. That patent describes a table-mounted retractor support comprising a first rod attached by a clamp to the side rail of an operating table, a second rod connected to the first rod by means of a second clamp, and a large unitary wishbone-shaped, rod, connected to the second rod by means of a third clamp. The wishbone-shaped rod has parallel arms to which are clamped various retractor blades.

The retractor support of U.S. Pat. No. 4,617,916 is a single-post device, and accordingly provides good exposure to the surgical site with a minimum of interference to the surgeon. The clamps by which the first rod is connected to the second rod and the second rod is connected to the wishbone are universal clamps which grasp circular rod sections. They provide for universal adjustment of the position of the wishbone-shaped retractor support structure. However, in practice, the apparatus is insufficiently secure unless a strong tightening force is applied to the clamps. Another difficulty with the apparatus of U.S. Pat. No. 4,617,916 is that the wishbone-shaped rod is too large to be sterilized conveniently, and is not easily disconnected from the clamp by which it is connected to the second rod.

The principle object of the present invention is to provide a single-post, table-mounted retractor support having improved strength and rigidity, while still having a range of adjustability such that it is acceptable to surgeons.

A further object of the invention is to provide a single-post, table-mounted retractor support which is more easily sterilized than prior retractor supports.

Further objects of the invention include the provision of a retractor support which is easily adjusted, in which the clamps are more easily and securely tightened, in which the clamps are more easily cleaned and sterilized, and in which the various parts are more easily detached from one another and assembled.

The surgical retractor support according to the invention comprises rod means for supporting a clamp means from a rigid support structure. Preferably, this rod means comprises a first, vertically extending rod, a clamp for securing the first rod to a rigid support structure such as the side rail of an operating table, a second rod adapted to extend horizontally from the first rod to a location over the operating table, and a clamping device for securing the second rod to the first rod. This clamping device is preferably designed to permit longitudinal adjustment of the second rod along its own axis, and to permit rotational adjustment of the second rod about the vertical axis of the first rod and also about an axis mutually perpendicular to the first and second rods.

Another clamp means is provided on the second rod at a position overlying the operating table. This clamp means has a first passage for receiving the second rod, and second and third passages. Screw means are provided on this clamp means for tightening all three passages simultaneously whereby rods in the three passages are tightly clamped in the passages simultaneously.

The retractor support utilizes a "split wishbone" structure, in which a first retractor support rod has an end section received in the second passage of the clamp means on the second rod and a second retractor support rod having an end section received in the third passage of the same clamp means.

The end sections of the first and second retractor support rods, and the first and second passages in the clamp means which receive them, have non-circular cross-sections cooperating to prevent rotation of the retractor support rods in the clamp passages. Preferably, the end sections of the first and second rods have flat surfaces on opposite sides, and the clamp passages which receive these end sections are rectangular in shape. The retractor support rods are preferably identical to each other, and have end sections which are parallel to each other, diverging intermediate sections, and parallel elongated sections overlying the patient. Retractors can be clamped both to the parallel elongated sections and to the intermediate sections.

The clamp by which the first and second rods are attached to each other is preferably substantially identical to, and interchangeable with, the clamp by which the retractor support rods are secured to the second rod. The portion of the second rod which extends into the clamp on the first rod, and the passage of the clamp through which it extends, preferably have non-circular cross-sections which prevent rotation of the second rod about its own axis.

The limitations on rotation of the second rod and on the two retractor support rods contribute to the rigidity and secure positioning of the retractor support structure without materially interfering with the free adjustability of the retractor support. The two separate rods which constitute the split wishbone structure are readily removed from their clamp, and can be replaced by rods of different sizes and shapes. Because the wishbone structure comprises two separate rods, each of relatively small size, the wishbone structure can be fit into a standard stainless steel sterilizing tray.

Further objects of the invention will be apparent from the following detailed description read in conjunction with the drawings. dr

BRIEF DESCRIPTION OF THE DRAWINGS

FIG. 2 is a top plan view of the retractor support;

FIG. 3 is a side elevation of the retractor support;

FIG. 4 is a fragmentary sectional view of one of the clamps of the retractor support;

DETAILED DESCRIPTION

Figure 1:
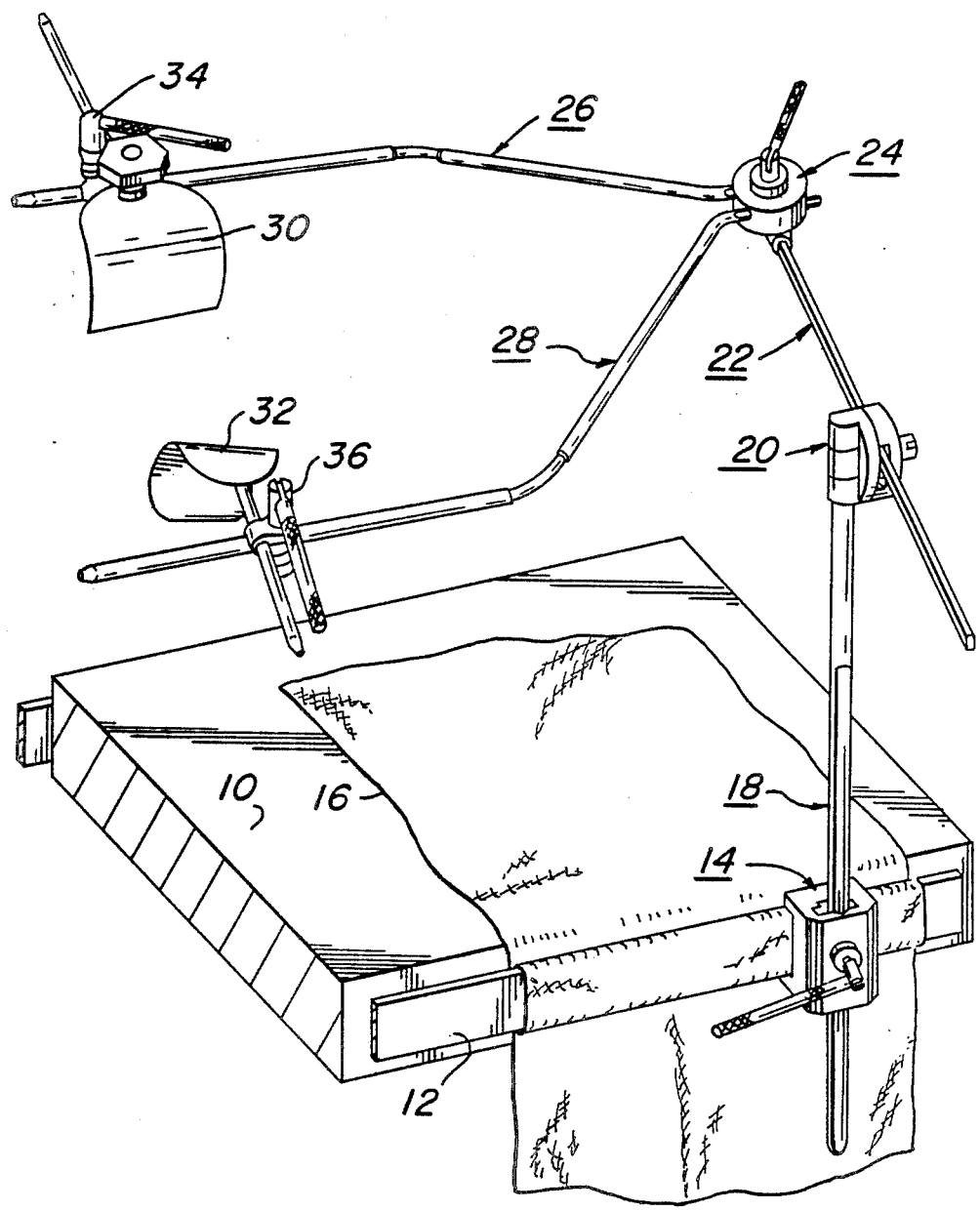
FIG. 1 is a fragmentary perspective view of an operating table having attached to it a retractor support in accordance with the invention.

FIG. 1 shows an operating table 10 having a pair of side rails. On side rail 12 is attached a clamp 14, which clamps over a surgical drape 16. Clamp 14 rigidly secures an upright rod 18 to rail 12. The height of rod 18, as well as its position along rail 12 are adjustable by loosening clamp 14.

At the upper end of rod 12 there is provided a clamp 20, which secures a second rod 22 in rigid relationship to upright rod 18. Rod 22 extends over the operating table, and has at its end a similar clamp 24. Clamp 24 holds a pair of arms 26 and 28, which together provide a wishbone-shaped structure for supporting various retractor blades such as blades 30 and 32, which are secured to rods 26 and 28 respectively by conventional clamps 34 and 36.

As shown in FIG. 2, wishbone arm 28 comprises an elongated first section 38 and an oblique second section 40 connected together by a reduced section 42, which allows clamps to be moved easily from one section to another without being completely detached from the arm. A third section 44 extends from section 40 into clamp 24. Section 44 has flat surfaces on its top and bottom sides, these flat surfaces cooperating with rectangular openings in clamp 24 to prevent rotation of arm 28 relative to the clamp. One such flat surface is shown at 46. Wishbone arm 26 is preferably identical to arm 28, and is secured in another rectangular opening in clamp 24 alongside end section 24 of arm 28.

As illustrated in FIG. 3, arm 28 has a compound curvature at reduced section 42 and at location 48 where section 40 meets section 44. This allows section 38 to be at a height lower than that of clamp 24, and thereby allows clearance, where necessary to accommodate the patient's face or chest, while holding section 38 in close proximity to the patient's abdomen. FIG. 4 shows the details of clamp 24. The clamp comprises a clamp body 50 and a clamping plate 52, which are secured together by a clamp screw 54 having a threaded shank 56. The shank is threaded into leg 58 of a T-shaped element having a tubular cross member 60 located in a gap between tubular elements 59 and 61 formed on the underside of clamp body 50. Extension 62, which is tightly secured by threads and thread-locking compound to the end of rod 22, extends into aligned cylindrical passages in elements 59, 60 and 61. A set screw 64 in clamp body 50 cooperates with groove 66 in extension 62 to prevent removal of extension 62 from the clamp body while allowing the clamp body to rotate about the extension when the clamping screw 54 is loosened.

The clamping screw is tightened by pivoted handle 68, there being a washer located between the head of the clamping screw and the clamping plate 52. A clearance is provided at 70 between the bottom wall of clamp body 50 and cross member 60 so that the cross member can be pulled in by clamp screw 54 to apply a shear force to extension 62 at the end of rod 22. This shear force securely locks clamp 24 against rotation relative to rod 22. At the same time, it presses clamping plate 52 downwardly toward the upper face of the clamp body 50. Clamping plate 52 has a pair of rectangular openings 72 and 74, which receive the short end sections of wishbone arms 26 and 28. The distance between the upper and lower flat faces on each wishbone arm (the upper face of arm 28 being face 46 in FIG. 2) should be slightly greater than the height of each rectangular opening, in order to allow the clamping plate to exert a clamping action on the wishbone arms. Tightening of clamping screw 54 tightens the clamp simultaneously on both wishbone arms and on extension 62 of rod 22. Even if one of the wishbone arms is missing, the clamp will still operate, being tightenable on one wishbone arm and on extension 62 of rod 22.

Figure 5:
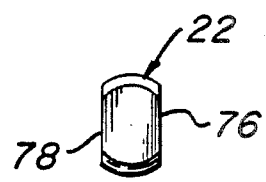
FIG. 5 is an end elevation showing the cross sectional shape of one of the retractor support rods.

Clamp 20, which secures rod 22 to rod 18, is substantially identical to clamp 24 and can be interchangeable with clamp 24. As shown in FIG. 3, clamp 20 receives rod 22 in one of the rectangular openings of its clamping plate, the other opening being unoccupied. Rod 22 is flattened on both of its sides, preferably throughout substantially its entire length, at faces 76 and 78, as shown in FIGS. 4 and 5. Here again, for proper clamping action, the distance between these opposed flat faces should be slightly greater than the depth of the rectangular opening in the clamping plate of clamp 20.

Upright rod 18 has similar flat faces, one of which is shown at 80 in FIG. 3. Rod 18 extends downwardly through side rail clamp 14, which is shown in detail in FIGS. 6 and 7. The side rail clamp has a fixed upper jaw 82 and a movable lower jaw 84. The lower jaw is moved by means of a threaded shaft 86, which has at its upper end a grooved cylindrical extension 88 received in a cylindrical opening in jaw 84, and held therein by cooperation of a groove 90 with a set screw 92, the set screw allowing rotation of extension 88 relative to jaw 84 while preventing disengagement of the jaw from the extension. Guide pins (not shown) may be provided on both sides of threaded shaft 86 to insure against jamming of the jaw. Movable jaw 84 is moved upwardly and downwardly by rotation of screw shaft 86 by means of pivoted handle 94. Upright rod 18 extends downwardly through opening 96 in clamp 14 (FIG. 7), and is secured in the clamp by a screw 98 operated by a pivoted handle 100.

Assembly of the retractor support on an operating table is carried out by first securing a rail clamp 14 on a side rail 12 on the operating table at the desired location, and thereafter assembling the other parts in a step-by-step manner. Post 18 and clamp 20 will normally be stored in assembled condition as will clamp 24 and rod 22. Thus, the unit consisting of rod 18 and clamp 20 can readily be secured to rail clamp 14, and the unit consisting of rod 22 and clamp 24 can readily be secured to clamp 20.

Figure 6:
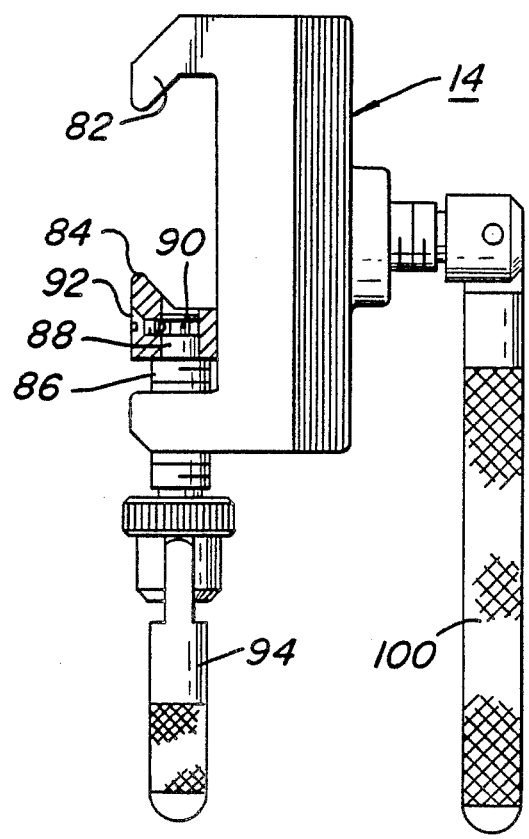
FIG. 6 is a side elevation of a clamp for securing the retractor support to the side rail of an operating table.
Figure 7:
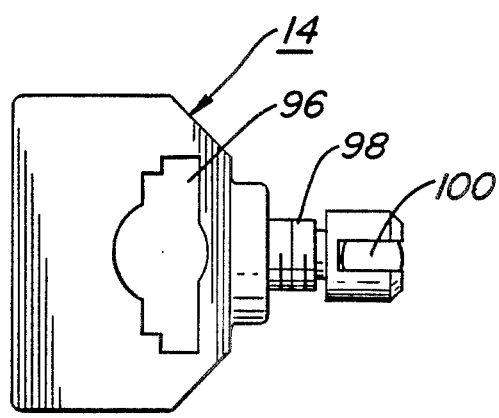
FIG. 7 is a top plan view of the clamp of FIG. 6.

Rod 18 and clamp 20 are secured, with clamp 20 at the desired height, by tightening handle 100 of rail clamp 14 (FIG. 6). Then, with clamp 20 in the loosened condition, rod 22 is inserted in clamp 20, and clamp 24 is brought to the desired location above the patient. Clamp 20 is then tightened.

Following tightening of clamp 20, the wishbone arms 26 and 28 are inserted into clamp 24, and brought to the desired position. Then, clamp 24 is tightened.

Wishbone arms of different sizes can be readily attached to clamp 24. For example, smaller wishbone arms can be used for juvenile patients. Clamp 24 will also accommodate a single wishbone arm on either side of the patient, and can be used to support retractor-holding arms in configurations other than the wishbone shape.

As the wishbone arms are individually detachable, they can be accommodated in a conventional 20 inch by 10.5 inch by 3.5 inch sterilizing tray along with the other components of the retractor support.

The flat walls of rod 22, and the flat walls of the end sections of the wishbone arms prevent rotation of these elements in their respective clamps. This contributes to the rigidity of the retractor support without materially limiting its adjustability. Forces applied to the retractor-supporting parts of the wishbone arms cannot cause rotation of these arms in clamp 24, nor can they cause rotation of rod 22 in clamp 20. Thus, such forces are less likely to cause loosening of the clamps than they are in the case of universal clamps. It has been found that the minor limitations on adjustability imposed by the flat sections and the corresponding rectangular openings in the clamps do not materially detract from the acceptability of the retractor support from the surgeon's point of view.

Height adjustment is accomplished primarily by adjusting the position of upright rod 18 in clamp 14, with further minor adjustments being effected by tilting of rod 22 in clamp 20 about the axis of the tightening screw of clamp 20, i.e. about an axis mutually perpendicular to rods 18 and 20.

Positioning of clamp 24 is achieved by longitudinal movement of rod 22 through clamp 20 and by rotation of clamp 20 about the axis of upright rod 18. Positioning of clamp 24 is also controlled by the positioning of clamp 14 on side rail 12 of the operating table.

After the position of clamp 24 is fixed by the tightening of clamps 14 and 20, and the wishbone arms are installed, the wishbone can be tilted about the axis of rod 22, and also rotated about the axis of the tightening screw of clamp 24, i.e. about an axis mutually perpendicular to rod 22 and to the short end sections of the wishbone arms held in clamp 24. Thus, the wishbone structure is tiltable about rod 22 and rotatable in the "plane" of the wishbone arms, i.e. the plane of the parallel, retractor-supporting sections one of which is section 38.

While the clamps 20 and 24 do not allow for universal movement because the rods which they clamp are not rotatable, they provide increased rigidity in the overall retractor support structure.

Additionally contributing to the rigidity of the structure is the clamp design by which the cylindrical rod sections to which the clamps are attached are gripped by a shear force, as depicted in FIG. 4. A relatively small torque applied to screw 54 by handle 68 results in a large shear force applied to rod section 62 by elements 59, 60 and 61. This shear force strongly resists rotation of clamp body 50 on rod section 62.

The clamps are interchangeable with each other, and preferably identical. They are easily assembled and disassembled for cleaning, simply by fully removing tightening screw 56, removing the clamping plate 52 and loosening set screw 64.

A number of modifications can be made to the apparatus described. For example, the wishbone arms can be designed with their short end sections perpendicular to, rather than parallel to their long end sections, i.e. with end section 44 extending perpendicular to end section 38. The short end sections would then extend into clamp 24 generally parallel to rod 22 rather than generally perpendicular to rod 22. While rods 18 and 22 are different from each other, as illustrated, they can also be identical to each other so that the same rod can be used as an upright post and as an intermediate connecting arm between the upright post and the wishbone structure.

I claim:

1. A support for surgical retractors comprising:
    rod means for supporting a clamp means from a rigid supporting structure;
    clamp means having a first passage for receiving the supporting rod means, and second and third passages, the clamp means also having screw means for tightening all three of said passages simultaneously whereby rods in said three passages are tightly clamped in said passages simultaneously;
    a first retractor support rod having an end section received in the second passage of the clamp means; and
    a second retractor support rod separate from said first retractor support rod and having an end section received in the third passage of the clamp means;
    the end sections of the retractor support rods being substantially parallel to each other, and the retractor support rods having intermediate sections diverging from each other and elongated sections extending substantially parallel to each other and connected to the end sections by the intermediate sections.

2. A support for surgical retractors according to claim 1 in which said clamp means comprises a clamp body, and in which said first passage comprises a pair of aligned passage sections in the clamp body, said passage sections having a gap between them, and a tubular element located in said gap and having a passage section aligned with said pair of passage sections of the clamp body, said screw means being arranged to urge said tubular element radially relative to said pair of aligned passage sections to apply a shear force to said supporting rod means.

3. A support for surgical retractors according to claim 2 in which the clamp means also comprises a clamp plate secured to the clamp body by said screw means, the second and third passages being defined by a pair of slots in said clamp plate and by a face of said clamp body.

4. A support for surgical retractors according to claim 2 in which a portion of the supporting rod means located in one of said aligned passage sections of said pair of aligned passage sections has a groove, and said clamp means having retaining means extending through said clamp body into said one of the aligned passage section and to said groove for preventing removal of said clamp means from said supporting rod means.

5. A support for surgical retractors according to claim 1 in which said end sections of the first and second retractor support rods and said second and third passages of the clamp means have non-circular cross-sections cooperating to prevent rotation of said retractor support rods in said passages.

6. A support for surgical retractors comprising:
    a first rod;
    means for securing the first rod to a rigid supporting structure;
    a second rod;
    first clamp means for securing the second rod to the first rod;
    second clamp means having a base defining a first passage for receiving the second rod, and a clamping plate defining with the base second and third passages located side-by-side and extending substantially parallel to each other, the second clamp means also having a single screw means for tightening the base and plate together whereby rods in said three passages are simultaneously clamped in said passages;

a first retractor support rod having an end section received in the second passage of the second clamp means; and a second retractor support rod having an end section received in the third passage of the second clamp means;

said end sections of the first and second retractor support rods and said second and third passages of the second clamp means having non-circular cross-sections cooperating to prevent rotation of said retractor support rods in said passages;

said end sections of said retractor support rods being substantially parallel to each other; and said retractor support rods having intermediate sections diverging from each other and elongated sections extending substantially parallel to each other and connected to said end sections by said intermediate sections.

7. A support for surgical retractors according to claim 6 in which the first clamp means has a passage for receiving a portion of the second rod and in which said portion of the second rod, and said passage of the first clamp means have non-circular cross-sections cooperating to prevent rotation of said second rod with respect to said first clamp means.

* * * * *